United States Patent
Glaug et al.

(10) Patent No.: US 6,478,786 B1
(45) Date of Patent: Nov. 12, 2002

(54) PROTECTIVE UNDERWEAR

(75) Inventors: Frank S. Glaug, Chester Springs, PA (US); Theresa A. Doubleday, Norristown, PA (US)

(73) Assignee: Tyco Healthcare Retail Services AG (CH)

(*) Notice: Subject to any disclaimer, the term of this patent is extended or adjusted under 35 U.S.C. 154(b) by 0 days.

(21) Appl. No.: 09/512,300

(22) Filed: Feb. 24, 2000

(51) Int. Cl.[7] ............................................. A61F 13/15
(52) U.S. Cl. ...................... 604/385.27; 604/385.29; 604/392
(58) Field of Search ................... 604/365, 368, 604/369, 375, 378, 383, 385.01, 385.08, 385.29, 396, 385.25, 392, 385.24–385.3

(56) References Cited

U.S. PATENT DOCUMENTS

| | | | |
|---|---|---|---|
| 4,641,381 A | 2/1987 | Heran et al. | |
| 4,646,362 A | 3/1987 | Heran et al. | |
| 4,938,753 A | 7/1990 | Van Gompel et al. | |
| 4,940,464 A | 7/1990 | Van Gompel et al. | |
| 5,163,932 A | 11/1992 | Nomura et al. | |
| 5,188,627 A | 2/1993 | Igaue et al. | |
| 5,236,430 A | 8/1993 | Bridges | |
| 5,246,433 A | 9/1993 | Hasse et al. | |
| 5,350,370 A | * 9/1994 | Jackson et al. | 604/367 |
| 5,464,401 A | 11/1995 | Hasse et al. | |
| 5,496,429 A | 3/1996 | Hasse et al. | |
| 5,520,673 A | 5/1996 | Yarbrough et al. | |
| 5,562,646 A | * 10/1996 | Goldman et al. | 604/368 |
| 5,569,234 A | 10/1996 | Buell et al. | |
| 5,645,543 A | 7/1997 | Nomura et al. | |
| 5,681,300 A | * 10/1997 | Ahr et al. | 604/367 |
| 5,685,874 A | 11/1997 | Buell et al. | |
| 5,735,839 A | 4/1998 | Kawaguchi et al. | |
| 5,746,731 A | 5/1998 | Hisada | |
| 5,749,865 A | 5/1998 | Yamamoto et al. | |
| 5,769,838 A | 6/1998 | Buell et al. | |
| 5,817,086 A | 10/1998 | Kling | |
| 5,817,087 A | * 10/1998 | Takabayashi et al. | 604/385.29 |
| 5,858,013 A | 1/1999 | Kling | |
| 5,876,390 A | 3/1999 | Hall et al. | |
| 5,876,392 A | 3/1999 | Hisada | |
| 5,879,341 A | * 3/1999 | Odorzynski | 604/367 |
| 5,947,948 A | 9/1999 | Roe et al. | |
| 6,017,336 A | * 1/2000 | Sauer | 604/385.1 |
| 6,306,122 B1 | * 10/2001 | Narawa et al. | 604/385.3 |

FOREIGN PATENT DOCUMENTS

| | | |
|---|---|---|
| EP | 0761194 | 3/1997 |
| EP | 0847739 | 6/1998 |
| WO | W.O.00/02511 | 1/2000 |

* cited by examiner

Primary Examiner—Dennis Ruhl
Assistant Examiner—Jamisue Webb
(74) Attorney, Agent, or Firm—Caesar, Rivise, Bernstein, Cohen & Pokotilow, Ltd.

(57) ABSTRACT

A protective underwear having a crotch portion, a waist portion, a front belly portion and a rear back portion. The waist, belly and back portions include plural transversely oriented elastic threads. The underwear includes an absorbent core. Longitudinally oriented elastic threads are located on opposite sides of the core and intersect the transverse elastic threads to enclose the core. The underwear includes a pair of leg openings, each of which has a first arcuate section, a second arcuate section, and an intermediate section. The first arcuate section includes at least one arcuate elastic thread, as does the second arcuate section. Those threads are spaced by a gap. A portion of the longitudinally oriented elastic threads on either side of the core is located closely adjacent a respective gap between the arcuate elastic threads to elasticize the leg openings.

29 Claims, 3 Drawing Sheets

PROTECTIVE UNDERWEAR

FIELD OF THE INVENTION

This invention relates generally to disposable absorbent articles for persons, children or adults, and more specifically to disposable protective underwear that can be readily pulled on and off the body, like underwear, and which provides improved absorbent functionality to prevent the soiling of outer garments by urine and/or feces.

BACKGROUND OF THE INVENTION

As populations continue to increase in longevity, incontinence, a problem of age presents a need for fluid control in undergarments. In particular, adult incontinence represents a transition from underwear to the use of some type of absorbent article to be added to the underwear or to completely replace it. For moderate-to-heavy incontinence needs a variety of disposable diaper designs are commercially available. Never the less certain deficiencies have been recognized in diapers that are currently found in the market place. For example, many of them, particularly high capacity designs, are thick and bulky, thus rendering concealment difficult. Moreover many of such prior art absorbent articles are complex in construction and are somewhat difficult to put on, e.g., require the use of elastic securement tabs. "See for example, U.S. Pat. No. 5,520,673 (Yarbrough et al.), U.S. Pat. No. 5,876,390 (Hall et al.), U.S. Pat. 5,817,086 (Kling), and U.S. Pat. No. 5,947,948 (Roe et al.), all of which disclose absorbent articles which may be of various shapes, such as rectangular, trapezoidal, T-shaped, I-shaped, hour-glass shaped, but which include various elastic components and/or other structural features, such as adhesive mounting tabs."

A recent development in the field is the so-called disposable training pants for children and disposable pants, shorts-type diapers, underwear or undergarments for adults. Such devices are constructed so that they can be easily pulled onto the wearer in a similar manner to the manner of donning briefs or shorts. "Examples of such easy-to-pull on devices are shown in the following U.S. Pat. No. 5,858,013 (Kling); U.S. Pat. No. 5,769,838 (Buell et al.); U.S. Pat. No. 5,749,865 (Yamamoto et al.); U.S. Pat. No. 5,746,731 (Hisada); U.S. Pat. No. 5,735,839 (Kawaguchi et al.); U.S. Pat. No. 5,685,874 (Buell et al.); U.S. Pat. No. 5,645,543 (Nomura et al.); U.S. Pat. No. 5,876,392 (Hisada); U.S. Pat. No. 5,569,234 (Buell et al.); U.S. Pat. No. 5,496,429 (Hasse et al.); U.S. Pat. No. 5,464,401 (Hasse et al.); U.S. Pat. No. 5,246,433 (Hasse et al.); U.S. Pat. No. 5,236,430 (Bridges); U.S. Pat. No. 5,188,627 (Igaue et al.); U.S. Pat. No. 4,940,464 (Van Gompel et al.); U.S. Pat. No. 4,938,753 (Van Gompel et al.); U.S. Pat. No. 5,163,932 (Nomura et al.); U.S. Pat. No. 4,646,362 (Heran et al.); and U.S. Pat. No. 4,641,381 (Heran et al.)." In addition there are some disposable absorbent pants or underwear available commercially from Kimberly Clark Company and Toyoeizai. All of the foregoing prior art devices make use of elasticized portions, typically about each leg and the waist. The leg elastic portions are provided to enable the device to closely conform to the wearer's anatomy and to deter the egress of fluids from the leg openings.

While the aforementioned prior art disposable protective undergarments are generally suitable for their intended purposes, they never the less leave something to be desired from the standpoint of resistance to leakage of fluid therefrom via gaps in their construction. Moreover, many prior art disposable protective undergarments are relatively complex in construction and difficult to manufacture.

OBJECTS OF THE INVENTION

Accordingly, it is a general object of this invention to provide protective underwear that addresses the needs of the prior art.

It is another object of this invention to provide protective underwear that can be readily pulled on or off;

It is another object of this invention to provide protective underwear that provides improved absorbent functionality and resistance to leakage;

It is another object of this invention to provide protective, leakage-resistant underwear which is disposable;

It is still another object of this invention to provide protective underwear that is readily concealable under clothing, provides a flexible, cloth-like feel, is resistant to leakage and is disposable when no longer needed.

It is still another object of this invention to provide protective underwear that can be manufactured efficiently.

SUMMARY OF THE INVENTION

A protective, e.g., disposable, underwear arranged to be worn by a person to trap and collect loose or liquid waste products of the person. The underwear is in the form of a pants-shaped chassis having a waist portion, a crotch portion and a pair of leg openings disposed on opposite sides of the chassis. The crotch portion is located between the leg openings and has a front section and a rear section. The waist portion has a front section and a rear section joined together at the sides of the chassis. The front and rear sections of the crotch portion merge together at the bottom of the chassis and are located opposite to the waist portion. Each of the leg openings has an arcuate upper section and an arcuate lower section.

The chassis comprises a hydrophobic or hydrophillic, e.g., a spunbond/meltblown/spunbond, non-woven material. The underwear also includes an insert comprising an insert sheet, a liquid permeable, e.g., a spunbond polypropylene, non-woven material, a liquid absorbent core, e.g., pulp and superabsorbent particulates disposed between a fluid acquisition layer and the liquid impermeable film, e.g., polyethylene film, and the heretofore mentioned fluid acquisition layer, e.g., a thru-air-bonded bicomponent fiber with a fast finish surfactant, between the core and the liquid permeable non-woven material insert sheet. The fluid acquisition layer may be eliminated, if desired. The insert also includes a liquid impermeable film, e.g., polyethylene film, located between the core and the chassis.

The waist portion of the chassis including plural transversely oriented elastic threads extending parallel to one another. These plural transversely oriented elastic threads encompass a substantial portion of the chassis from the waist portion to a point adjacent the crotch portion. The chassis also includes a pair of longitudinally oriented elastic threads intersecting a least one of the transversely oriented elastic threads of the front section of the waist portion and intersecting at least one of the transversely oriented elastic threads of the rear section of the waist portion to form an enclosed compartment for the liquid absorbent core to prevent the egress of liquid therefrom.

The upper section of each of the leg openings is located adjacent the waist portion and is elasticized by at least one arcuate elastic thread. Portions of the longitudinally oriented elastic threads are located very close to the lower sections of the leg openings to elasticize the lower sections of the leg openings, whereupon the leg openings closely conform about the leg of the person.

DETAILED DESCRIPTION OF THE PREFERRED EMBODIMENT

Figure 1:
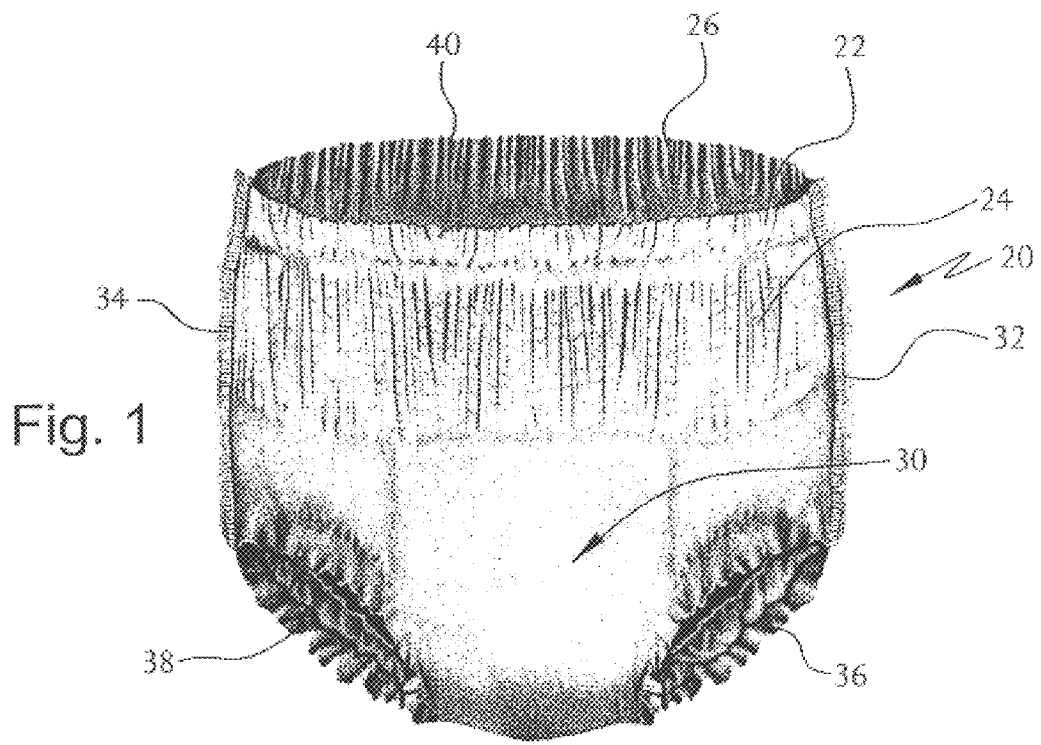
FIG. 1 is a front isometric view of a protective undergarment, e.g., brief, constructed in accordance with this invention.

Referring now to the various figures of the drawing wherein like reference characters refer to like parts, there is shown in FIG. 1 a disposable protective garment 20 constructed in accordance with one embodiment of this invention. The undergarment of FIG. 1 is in the form of a pants or briefs and is particularly constructed to enable it to be readily pulled on or pulled off, like conventional underwear.

Figure 2:
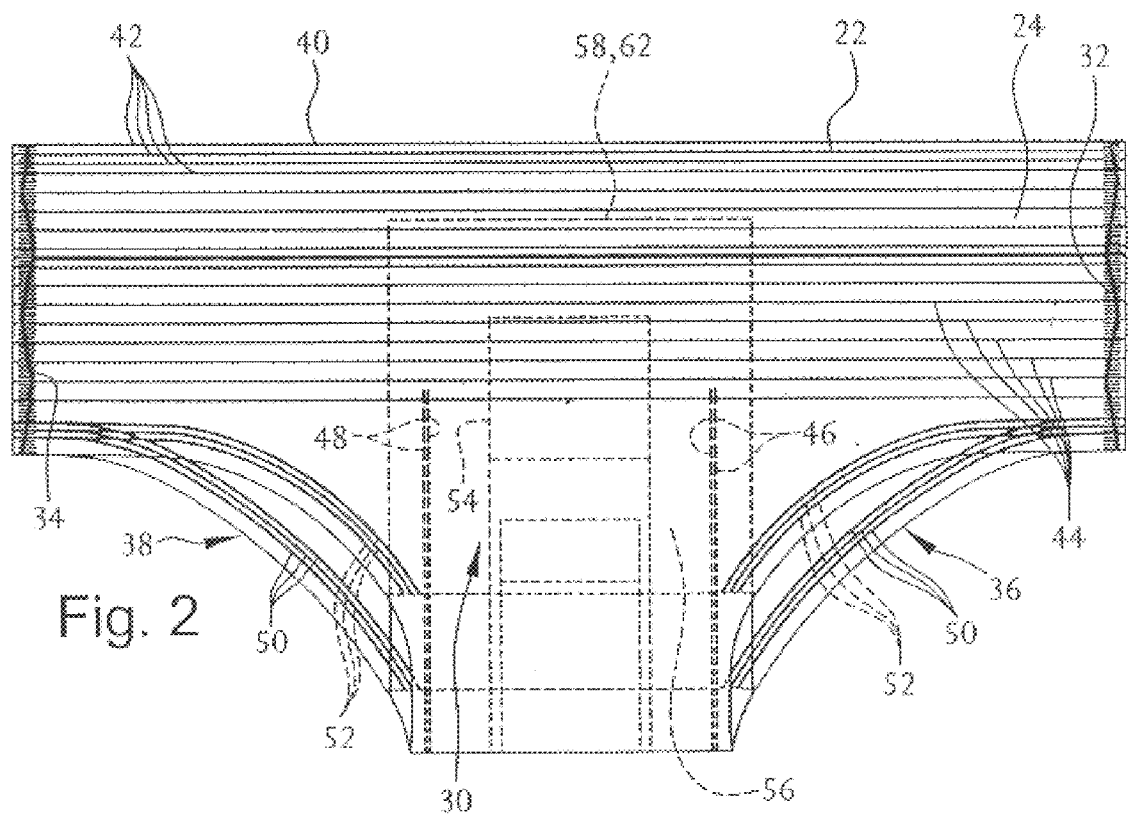
FIG. 2 is front plan view of the undergarment shown in FIG. 1.

The briefs basically comprise a cloth-like chassis made of a front waist section 22, a belly section 24 (located below the front waist section), a rear waist section 26, a rear back section 28 (located below the rear waist section), and an intermediate crotch section 30. The front and rear waist sections 22 and 26, respectively, and the belly and back sections 24 and 28, respectively, are secured together, e.g., welded or glued along respective side seams 32 and 34 of the chassis. As can be seen in FIG. 2, the side seams include short horizontal seal lines and a zig-zag seal line.

The chassis also includes a pair of leg openings 36 and 38 disposed on opposite sides of the crotch section 30. The leg openings are elasticized, as will be described later. The top edge of the chassis, i.e., the front waist section and rear waist section, is denoted by the reference number 40.

Figure 4:
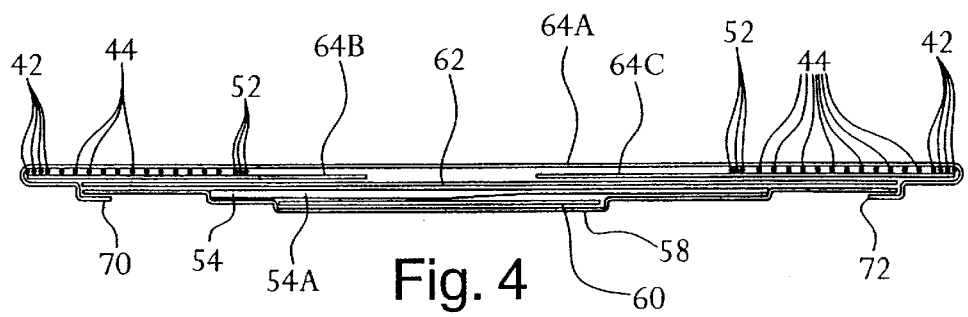
FIG. 4 is a sectional view taken along line 4—4 of FIG. 3.
Figure 3:
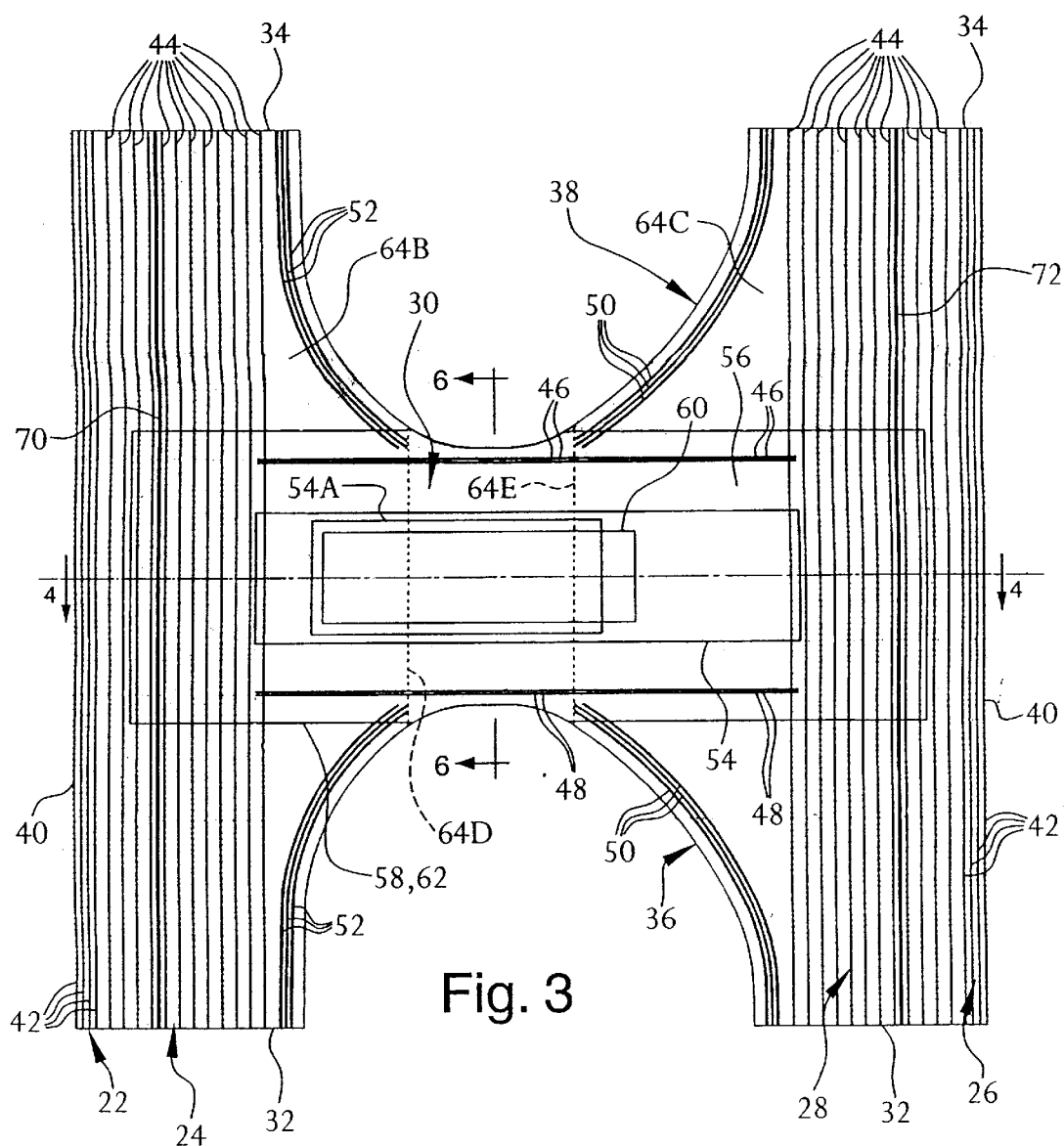
FIG. 3 is a top plan view of the various components of the undergarment of FIG. 1 shown laid flat before the side seams are formed to produce the brief.

As will be discussed in detail later, and as can be seen in FIGS. 3 and 4, the chassis is composed of a single outer sheet (sometimes referred to as the "backsheet") of a cloth-like, non-woven, breathable material having a generally rectangular shape with a pair of asymmetrically U-shaped recesses cut in the sides thereof, and a pair of inner sheets, also of the same material.

"The inner sheets correspond in shape and size to the end portions of the outer sheet and are glued on the inner surface of the outer sheet so that there is a gap between the two inner sheets at the center of the crotch portion."

The undergarment 20, and in particular, its chassis, is elasticized to enable it to be readily pulled on and pulled off, and when in place to conforms to the body of the wearer, while also precluding the egress of any liquid such as urine or loose feces from it. In particular, the chassis is elasticized by the use of a plurality of elastic fibers or filaments which are glued in place in the chassis between the outer sheet and the two inner sheets, as will be described later. As best seen in FIG. 2, a first group or plurality of elastic filaments or fibers 42 are included in the chassis and extend across the chassis from side to side of the front waist section and a similar group of fibers are included in a similar manner in the rear waist section. These transversely oriented elastic fibers are closely spaced parallel to one another, e.g., 0.25 inch. A second group or plurality of identical fibers are also included in the chassis and extend across the chassis from side to side in the front belly section and a similar group of fibers are included in a similar manner in the rear back section. The transversely oriented, second group of fibers are denoted by the reference number 44 and the fibers in each such group are also equidistantly spaced from one another, but at a greater spacing than the fibers 42 of the first groups, e.g., at 0.5 inch spacing.

The fibers are included in the chassis under tension (they are stretched) and are placed on the inner surface of the outer sheet of the chassis in the front waist and belly area of the front of the chassis and in the rear waist and back section of the rear of the chassis. The two inner sheets of the chassis are then applied over the tensioned fibers and the backsheet and adhesively secured thereto by any suitable adhesive to seal the fibers therebetween.

As best seen in FIG. 3 and FIG. 4, the backsheet or outer sheet of the chassis, and which is designated by the reference number 64A, has a generally rectangular shape with a pair of slightly asymmetrical U-shaped recesses cut into its sides and disposed opposite each other. The U-shaped recesses form the leg openings 36 and 38 when the sides 32 and 34 of the chassis are secured together. One of the inner sheets, designated by the reference number 64B, is identical in shape to the portion of the backsheet 64A forming the front of the chassis. The inner sheet 64B when disposed over the corresponding part of the backsheet 64A only extends to a point before the nadir of the U-shaped recesses forming the leg openings. In particular, the sheet 64B terminates at a linear edge 64D (shown by the dotted line in FIG. 3). The other inner sheet 64C is correspondingly shaped to the portion of backsheet 64A forming the rear of the chassis and terminates along a linear edge 64E (shown by the phantom line in FIG. 3). Thus, there is a gap between the two inner sheets 64B and 64C, i.e., between the edges 64D and 64E, whereupon at the location of the gap the chassis only consists of a single layer, namely, the outer layer 64A.

The material forming the chassis can be any suitable material. In the interest of wearing comfort, it is preferably non-woven, cloth-like breathable material such as spunbond/meltblown/spunbond polypropylene at 15 gsm available from Avgol of Holon, Israel. The material making up the chassis sheets may be a polylaminate, e.g., polyfilm bonded to a non-woven material. The adhesive for securing the sheets 64A–64C together with the elastic fibers interposed therebetween, is a construction adhesive, e.g., available from National Starch and Chemical Company of Bridgewater, N.J.

The underwear (briefs) also include an insert, to be described later, which is adhesively secured, on the inner surface of the chassis, i.e., on the portion of the chassis in the crotch area covering portions of the two chassis inner sheets 64B and 64C and portions of the gap between those two inner sheets. The insert includes a liquid-absorbent core 54 for absorbing urine.

As should be appreciated by those skilled in the art, when all of the components making up the undergarment 20 have been assembled and the sides of the chassis as described earlier are sealed and tension is released on the elastic fibers, the fibers of the chassis contract, thereby causing the upper portion of the chassis, that is the waist, belly and back sections to shrink in diameter and to cause the chassis to "pucker" like shown in FIG. 1.

In addition to the transversely oriented elastic fibers 42 and 44, the chassis also includes other elastic fibers between the outer sheet 64A and the two inner sheets 64B and 64C to help in elasticizing the leg openings. These other elastic fibers cooperate with some of the fibers 44 in the belly and back sections of the chassis to form a gasketed compartment for the absorbent core to prevent the egress of liquid therefrom. This gasketed compartment will be described later.

As mentioned earlier, the leg openings 36 and 38 are elasticized. To that end, the chassis includes three arcuate elastic fibers 50 located between the chassis' outer sheet 64A and the chassis' inner sheet 64C that forms the rear portion of the chassis and which is adjacent the recess forming the leg opening 36 (see FIG. 3). Three similar arcuate elastic fibers 50 are located between the chassis' outer sheet 64A and the chassis' inner sheet 64C that forms the rear portion of the chassis adjacent the recess forming the leg opening 38. Three similar arcuate elastic fibers 52 are located between the chassis' outer sheet 64A and the chassis inner sheet 64B forming the front portion of the chassis adjacent the portion of the recess forming the leg opening 36. Similarly, three arcuate fibers 52 are located between the chassis' outer sheet 64A and the chassis' inner sheet 64B forming the front portion of the chassis along the portion of the recess forming the leg opening 38.

The insert for the underwear includes two pairs of linear longitudinally oriented elastic fibers 46 and 48. When the insert is in place on the chassis, the pair of fibers 48 of the insert are located adjacent the arcuate elastic fibers 50 and 52 forming the leg opening 36 to fill the gap between those arcuate fibers to effectively elasticize the entire periphery of that leg opening. In a similar manner, the longitudinally extending elastic fibers 46 of the insert are located immediately adjacent the arcuate elastic fibers 50 and 52 forming the leg opening 38 to fill the gap between those arcuate elastic fibers to effectively elasticize the entire periphery of that leg opening. In particular, the central portion of the linear elastic fibers 48 coact with the arcuate fibers 50 and 52 to effectively elasticize the leg opening 36 about its entire periphery, while the longitudinally extending linear fibers 46 coact with the arcuate fibers 50 and 52 to effectively completely elasticize the leg opening 38. Thus, when the protective underwear is in place on the wearer, the elastic fibers making up each leg opening closely conforms the chassis contiguous therewith about the leg of the wearer to engage the skin and form a liquid resistant seal. This action deters the leakage of urine and/or loose feces out of the leg openings.

In order to facilitate the correct orientation of the undergarment to put it on, since it is asymmetrical (the rear portion is longer/higher than the front portion), at least some of the elastic fibers of either the front or back of the undergarment are distinctively colored to be readily discernable from the color of the chassis material, e.g., the fibers 42 and 44 in the rear waist and/or rear back sections may be colored blue or green or any other color to contrast with the white color of the chassis, thereby enabling a person to readily determine what is the front and what is the rear of the undergarment so that it can be put on properly.

To put the undergarment on all that is required is for the user to orient the garment in the appropriate direction and to stretch the waist and contiguous upper portion of the chassis to enable his or her leg to be extended through the appropriate leg opening and then through the other leg opening. Then the user can pull the undergarment up so that its waist is located at the wearer's waist and its crotch is located over the wearer's crotch. Thus, the underwear can be put on as easily as any conventional undergarment. Removal of the undergarment is accomplished in a similar conventional manner.

Figure 5:
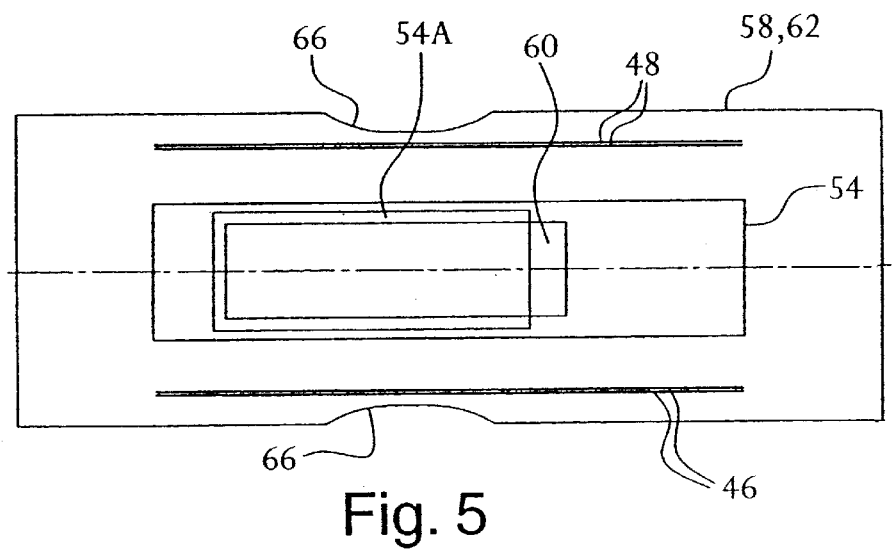
FIG. 5 is a top plan view of a portion of the undergarment of FIG. 1.
Figure 6:
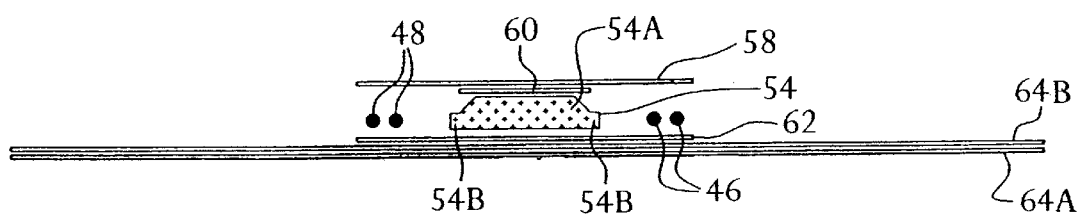
FIG. 6 is a transverse sectional view taken through the garment along line 6—6 of FIG. 3 before the formation of the side seams.

Referring now to FIGS. 4–6, the details of the construction of the insert for the chassis will now be discussed. In particular, the insert comprises a liquid pervious insert sheet or cover sheet 58, a fluid acquisition layer 60, the heretofore identified liquid absorbent core 54, and a liquid impervious barrier sheet or layer 62. The core 54 is located in a compartment 56 to be described later and which is formed between the insert sheet 58 and the sheets 64A, 64B and 64C making up the chassis, as well as certain of the heretofore identified elastic fibers. In particular, as best seen in FIG. 5, the compartment 56 is defined by the intersection of the longitudinally oriented elastic fiber pairs 46 and 48 and certain ones of the transversely oriented elastic fibers 44 of the belly and back sections of the chassis. These intersecting fibers closely surround the core to effectively form a gasket about the periphery of the core to prevent leakage of urine out of the core.

In order to prevent the egress of urine out through the non-woven sheets of the chassis, the chassis' insert also includes the heretofore identified barrier sheet or layer 62. The barrier sheet 62 is interposed between the core 54 and the chassis. The barrier sheet 64 is formed of a liquid impervious material, e.g., a microporous polyfilm which is vapor permeable (breathable). In the embodiment shown herein, the barrier sheet 62 is of the same generally rectangular shape and size as the cover or insert sheet 58 and is located in the crotch section of the undergarment within the compartment 56, as best seen in FIG. 5. In accordance with one exemplary embodiment, the barrier sheet 62 is formed of a film of 0.6 mil polyethylene available from Huntsman Packaging of Salt Lake City, Utah.

The core 54 is disposed on top of the barrier sheet 62. In the embodiment shown herein, the core is of a generally rectangular shape having a central portion 54A of increased thickness as compared to its sides marginal portions 54B as best seen in FIG. 6. Moreover, the thickened central portion 54A of the core tapers from the front to the rear as best seen in FIG. 4. These structural features of the core and its location ensures that the maximum thickness of the core is located at the anatomical position at which the urine insult from the person will be initiated.

The core can be formed of any suitable material(s), e.g., an airlaid composite, containing pulp, superabsorbent particulates and/or fibers, and binders. The binders may be chemical or thermal.

In accordance with one exemplary embodiment, the core 54 is made up of mainly cellulosic fibers, e.g., wood pulp fluff made of up bleached sulfate wood pulp containing softwood fibers, such as that available from International Paper of Tuxedo, N.Y., co-mingled with hydrogel polymer particulates (known as Super Absorbent Polymer or "SAP") such as cross-linked polyacrylate ASAP 2260 available from Chemdal Corporation of Palatine, Ill. If desired, these materials may be optionally enwrapped in tissue. The amount of each absorbent material and SAP/fluff ratio depends on the size of the protective underwear, whether it is used for children (e.g., training pants) or for adults, and whether or not a transfer or fluid acquisition layer component is to be included in the insert. In this regard, the fluid acquisition layer 60 as shown herein may be omitted from the underwear 20, if desired. However, in the embodiment shown the acquisition layer 60 is used between the absorbent layer 54 and the insert sheet or layer 58. The fluid acquisition layer 60 is located over the thickened portion of the core, i.e., the portion where the urine insult will be initiated. As is known, the fluid acquisition layer 60 serves to manage, transport, accommodate and/or direct high volumes and flow rates of urine into the core.

The fluid acquisition layer can be thru-air bonded/carded web, a spunbond bicomponent non-woven web, a web of crosslink cellulosic fibers, apertured 3D (three dimensional) film or the like. One particularly suitable material is a thru-air bonded bicomponent with a fast finish surfactant available from PGI Non-wovens of Landisville, N.J. and has an overall basis weight of 40 gsm. The bicomponent fibers are made of a polypropylene inner core and a polyethylene outer sheath. The fluid-acquisition layer 60 may be adhesively secured in place by any suitable construction adhesive or hydrophillic adhesive, such as Cycloflex adhesive available from National Starch and Chemical of Bridgewater, N.J. If desired, the core 54 may also be held in place by a similar adhesive.

As best seen in FIG. 5, the insert sheet 58 is a generally rectangular member having a pair of arcuate cut-outs 66 which are of the same size and shape as the nadir of the asymmetrical U-shaped recesses forming the leg openings 36 and 38. In accordance with one exemplary embodiment of the underwear 20, the insert sheet 58 is a non-woven spunbond polypropylene of 15 gsm available from Avgol of Holon, Israel, wherein the non-woven material is zone coated with its longitudinal central area being hydrophillic and its two longitudinal side areas being hydrophobic. The insert sheet may also be formed of an apertured three dimensional film or a combination of such film and a non-woven material. The insert sheet 58 is of the same size and shape as the barrier sheet 62 and is disposed thereover. The insert sheet 58 is glued to the barrier sheet with the acquisition layer 60 and the core 54 interposed therebetween and completely about the perimeter of the core and acquisition layer. The top and bottom edges 70 and 72 of the chassis' backsheet 64A are folded over the end marginal edges of the insert sheet 58 as shown in FIG. 4 and are adhesively secured in place thereat.

As discussed earlier, the longitudinally extending elastic fibers 46 and 48 are arranged to intersect with selected ones of the transversely extending fibers 44 to form the heretofore mentioned compartment for the core. To that end, as best seen in FIGS. 5 and 6, two pair of the heretofore identified longitudinally elastic fibers 46 and 48 are located on opposite sides of the core 54 between the insert sheet 58 and the barrier sheet 62. The fibers of each pair are linear and extend for a major length of the insert sheet/barrier sheet so that when located in place, they intersect several of the transversely extending elastic fibers 44 of the belly section and the back section as best seen in FIGS. 2 and 3. Thus, the core 54 is located within a compartment 56 bounded by those intersecting elastic fibers, with the fibers serving as a "gasket" to prevent outward or lateral migration of urine from the core.

In accordance with one exemplary embodiment of the invention, the transversely extending fibers 42 and 44 are formed of 620 LYCRA® available from E.I. DuPont de Nemours of Wilmington, Del. The longitudinally extending fibers 46 and 48 are formed of the same material. However, the arcuate fibers 50 and 52 are formed of a different material, e.g., 920 LYCRA® available from E.I. DuPont de Nemours of Wilmington, Del.

As should be appreciated from the foregoing, the use of linear elastic fibers and arcuate elastic fibers for cooperation with each other to effectively form a complete peripheral seal to elasticize the leg openings in lieu of completely encircling the leg openings with an arcuate elastic fiber expedites the manufacture of the protective underwear on a continuous basis, e.g., where blanks forming the chassis are carried in a web past stations for applying the filaments, and other components and gluing the components together. Moreover, by making use of the linearly extending longitudinal elastic fibers to form a portion of the leg openings, one is able also to use those fibers as a portion of a gasketing system to intersect the transverse fibers to form the heretofore identified sealed compartment to prevent leakage of urine from the core, a feature unknown to the prior art.

It should be pointed out at this juncture that the materials as described heretofore to make up the underwear are merely exemplary of numerous materials that can be used for the various components. Thus, other conventional materials can be used for the chassis, the insert, its components, and the elastic threads or fibers.

Without further elaboration, the foregoing will so fully illustrate our invention that others may, by applying current or future knowledge, adopt the same for use under various conditions of service.

We claim:

1. A protective underwear arranged to be worn by a person having legs to trap and collect loose or liquid waste products of the person, said underwear comprising a pants-shaped chassis having a front waist portion, a belly portion, a rear waist portion, a rear back portion, a crotch portion, and a pair of leg openings disposed on opposite sides of said chassis, with said crotch portion being located between said leg openings and having a front section and a rear section, said front waist portion and said rear waist portion being joined together at the sides of said chassis, said belly portion and said rear back portion being joined together at the sides of said chassis, said underwear additionally comprising an insert having an insert sheet and a liquid absorbent core disposed between said insert sheet and said chassis, each of said leg openings having a first arcuate section, a second arcuate section, and an intermediate section, said first arcuate section having an inner end located adjacent said core, said second arcuate section having an inner end located adjacent said core, said intermediate section being located adjacent said core between said inner ends of said first and second arcuate sections, said front waist portion of said chassis including plural transversely oriented elastic threads extending parallel to one another, said plural transversely oriented elastic threads encompassing a substantial portion of said chassis from said front waist portion into said belly portion to a point adjacent said crotch portion, said underwear additionally comprising at least two generally linear longitudinally oriented elastic threads, with respective ones of said longitudinally oriented elastic threads extending on opposite sides of said core outside margins of said core and between said leg openings, said longitudinally oriented elastic threads intersecting at least one of said transversely oriented elastic threads of said belly portion and intersecting at least one of said transversely oriented elastic threads of said rear back portion to form an enclosed, rectangular gasketed compartment for said liquid absorbent core closely conforming to the perimeter of said core to prevent the egress of liquid therefrom, said first arcuate section of each of said leg openings being elasticized by at least one arcuate elastic thread, said second arcuate section of each of said leg openings being elasticized by at least one arcuate elastic thread, said at least one elastic thread of said first arcuate section terminating at an inner end, said at least one elastic thread of said second arcuate section terminating at an inner end, said inner ends being spaced from each other by a gap, said gap being located at said intermediate section, and wherein a portion of one of said longitudinally oriented elastic threads is located very close to said gap in said intermediate section of one of said leg openings, and a portion of the other of said longitudinally oriented elastic threads is located very close to said gap in said intermediate section of the other of said leg openings, whereupon said longitudinally oriented elastic threads cooperate with said arcuate elastic threads to elasticize said leg openings to enable said leg openings to closely conform about the legs of the person.

2. The protective underwear of claim 1 wherein said compartment has an area, wherein said insert sheet and said chassis are liquid permeable, and wherein said underwear additionally comprises a liquid impermeable layer disposed between said core and said chassis and encompassing said area of said compartment.

3. The protective underwear of claim 1 wherein said underwear additionally comprises a fluid acquisition layer located between said insert sheet and said liquid absorbent core within said compartment.

4. The protective underwear of claim 1 wherein said transversely oriented elastic threads comprise two first groups and two second groups, a first one of said two first groups being located in said front waist portion and a second one of said first two groups being located in said rear waist portion, a first one of said two second groups being located in said belly portion and a second one of said two second groups being located in said rear back portion, and wherein said transversely oriented threads of said first groups are spaced closer to one another than said transversely oriented threads of said second groups.

5. The protective underwear of claim 1 wherein said underwear includes a front section comprising said front waist portion and said belly portion and a rear section comprising said rear waist portion and said rear back portion and wherein portions of said transversely extending threads that are located in either said front section or said rear section are of a distinctive color as compared to said chassis to be readily visible by the person.

6. The protective underwear of claim 1 wherein said compartment has a periphery and said insert sheet and said chassis are bonded about said periphery of said compartment.

7. The protective underwear of claim 1 wherein said core is of a generally rectangular shape.

8. The protective underwear of claim 1 wherein said chassis comprises a backsheet and two inner sheets adhesively secured to said backsheet, said inner sheets being of non-woven material.

9. The protective underwear of claim 1 wherein said transversely oriented elastic threads and said longitudinally oriented linear elastic threads are of the same material.

10. The protective underwear of claim 9 wherein said arcuate elastic threads are of a different material than said transversely oriented elastic threads.

11. The protective underwear of claim 1 wherein said chassis material is a polylaminate.

12. The protective underwear of claim 11 wherein said polylaminate is polyfilm laminated to a non-woven material.

13. The protective underwear of claim 1 wherein said insert sheet comprises a non-woven material.

14. The protective underwear of claim 13 wherein said non-woven material is spunbond polypropylene.

15. The protective underwear of claim 13 where said non-woven material is zone-coated spunbond polypropylene, having a longitudinal central area that is hydrophillic and two longitudinal side areas that are hydrophobic.

16. The protective underwear of claim 1 wherein said core is formed of a highly moisture absorbent material.

17. The protective underwear of claim 16 wherein said core is formed of pulp and a superabsorbent particulate.

18. The protective underwear of claim 16 wherein said core is formed of an airlaid composite, containing pulp, superabsorbent particulates and/or fibers, and at least one binder.

19. The protective underwear of claim 18 wherein said at least one binder is selected from the group consisting of chemical and thermal binders.

20. The protective underwear of claim 1 wherein said chassis comprises a non-woven material.

21. The protective underwear of claim 20 wherein said non-woven material is a spunbond polypropylene material.

22. The protective underwear of claim 20 wherein said non-woven material is spunbond/meltblown/spunbond polypropylene.

23. The protective underwear of claim 22 wherein said insert sheet is an apertured three dimensional film or a combination of such a film and a non-woven material.

24. The protective underwear of claim 23 wherein said compartment has an area, and wherein said underwear additionally comprises a liquid impermeable layer disposed between said core and said chassis and encompassing said area of said compartment.

25. The protective underwear of claim 24 wherein said liquid impermeable layer is microporous polyfilm, which is vapor permeable.

26. The protective underwear of claim 24 wherein said liquid impermeable layer is polyethylene film.

27. The protective underwear of claim 26 wherein said underwear additionally comprises a fluid acquisition layer located between said insert sheet and said core.

28. The protective underwear of claim 27 wherein said fluid acquisition layer comprises a thru-air-bonded, bicomponent fiber with a fast finish surfactant.

29. The protective underwear of claim 26 wherein said fluid acquisition layer comprises an apertured three dimensional film or a combination of such film and a non-woven material.

* * * * *